United States Patent [19]
Bernard et al.

[11] Patent Number: 5,985,841
[45] Date of Patent: Nov. 16, 1999

[54] DEOXYGLUCOPYRANOSIDE COMPOUNDS FOR INDUCING/STIMULATING HAIR GROWTH AND/OR RETARDING HAIR LOSS

[75] Inventors: Daniel Bernard, Courbevoie; Henri-Jean Caupin, Versailles; Serge Petit, Cusy, all of France

[73] Assignee: ELF Atochem S.A., Puteau, France

[21] Appl. No.: 09/055,270

[22] Filed: Apr. 6, 1998

[30] Foreign Application Priority Data

Apr. 4, 1997 [FR] France .................................. 97 04145

[51] Int. Cl.$^6$ ..................................................... A61K 31/70
[52] U.S. Cl. .............................................. 514/23; 514/880
[58] Field of Search ................................................ 514/23

[56] References Cited

U.S. PATENT DOCUMENTS 5,728,661 3/1998 Petit et al. ............................... 510/126

FOREIGN PATENT DOCUMENTS 0 348 184 12/1989 European Pat. Off. .
0 769 499 4/1997 European Pat. Off. .

OTHER PUBLICATIONS

CA 73:317, Ishizuka et al Jap J Exp Med 39(3) 321–5 1969.
CA 70:84404, OpenKamp et al, Biochim Biophip. Acta 176(2), 298 305 1969.

*Primary Examiner*—Rebecca Cook
*Attorney, Agent, or Firm*—Burns, Doane, Swecker & Mathis, L.L.P.

[57] ABSTRACT

A regimen for inducing/stimulating hair growth and/or retarding hair loss on an individual in need of such treatment comprises topically applying to the affected hair and/or scalp of such individual, a hair growth stimulating and/or hair loss retarding effective amount of at least one 2,3-dihydroxypropyl-2-(1-oxohydrocarbyl) amino-2-deoxyglucopyranoside having the structural formula:

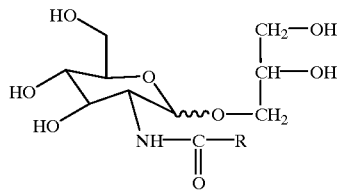

in which R is a linear or branched, saturated or unsaturated hydrocarbon radical having from 5 to 21 carbon atoms.

8 Claims, No Drawings

DEOXYGLUCOPYRANOSIDE COMPOUNDS FOR INDUCING/STIMULATING HAIR GROWTH AND/OR RETARDING HAIR LOSS

CROSS-REFERENCE TO PRIORITY APPLICATION

This application claims priority under 35 U.S.C. §119 of FR-97/04145, filed Apr. 4, 1997, hereby expressly incorporated by reference.

BACKGROUND OF THE INVENTION

1. Technical Field of the Invention

The present invention relates to novel cosmetic and/or therapeutic compositions for topical application to mammalian subjects which are intended to induce and stimulate hair growth and/or to slow down or retard hair loss.

2. Description of the Prior Art

In human subjects, hair growth and hair renewal are principally determined by the activity of the hair follicles. This activity is cyclic and essentially entails three phases, namely, the anagenic, catagenic and telogenic phases. The anagenic active phase, or growth phase, which lasts for several years and during which the hair elongates, is followed by a transitional catagenic phase of about two weeks, during which the follicle regresses and becomes involuted, after which there is a rest phase or telogenic phase which lasts about 70 days, at the end of which the hair falls out. Following this, another cycle begins. The follicles are genetically programmed to produce about 25 regrowths, and a normal cycle lasts on average for five years, thereby permitting permanent renewal of the head of hair during a lifetime. Out of the approximately 150,000 hairs which make up a head of hair, usually about 80 thus fall out each day, which will be replaced in a few months.

Early thinning of the head of hair, or alopecia, which occurs in certain individuals, has both genetic and hormonal implications. The genetic aspect is seen when it corresponds to the "bald nature" which is transmitted from father to son, and more rarely from mother to son, and is very probably carried by several genes. The hormonal aspect is seen when it is due to binding to molecular receptors in the root of certain enzymatic degradation products of testosterone, the principal male hormone, these aspects developing, for example, following stress. This results in an accumulation of collagen in the collective sheath (fibrosis), leading to a slowing-down in the growth of the hair, and later its death. The disturbances in hair renewal are reflected, in a first stage, by acceleration of the frequency of the cycles, at the expense of the quality of the hair and then of the amount thereof: there is gradual thinning of the head of hair by regression of the so-called "end" hairs at the duvet stage, and finally the moment is reached at which there is no further regrowth. In men, the areas affected are principally the temporal or frontal areas and the occipital region. In women, diffuse alopecia of the vertex is observed.

More than 11 million men in France alone are directly affected by hair loss. Thus, compounds and compositions which make it possible to eliminate or reduce the effect of alopecia, and especially of inducing or stimulating hair growth or of decreasing hair loss, have long been sought in the cosmetic and pharmaceutical industries.

In approaches featuring a carbohydrate base, the synergistic action of mono-, di- and oligosaccharides with various active agents has recently been described; for example fructose in combination with polyvinylpyrrolidone (see JP-08,040,846), trehalose with chitosan and various natural active agents (see JP-08,020,514), the hydrolysis products of alginic acid with a blood circulation accelerator and a cell activator (see WO-96/07393), starch in combination with zinc oxide and boric acid (see WO-95/35086), and glucose or fructose in combination with globular cereal proteins or hydrolyzates thereof (see FR-27/04751).

Oligosaccharides containing at least one disaccharide structural unit comprising a uronic residue and a hexosamine residue (see EP-211,610) have also been described.

Aldonolactones or hexosaccharic acids too have been described, for example D-fucono-1,5-lactone (see EP-531,111), lactam forms of saccharides, for example L-arabino-1,5-lactam and D-glucurono-6,3-lactam (see EP-0,334,586), a cellobione/lactone polymer obtained via its derivation into N-p-vinyl benzyl D-cellobionamide (see JP-05,043,418).

Glycosides of ergosterol (see JP-07,101,835 and JP-07,109,293), of stigmasterol (see JP-07,138,181), of stigmastanol (see JP-07,109,294) and p-β-D-glucopyranosyloxycinnamic acid (see JP-07,258,042) or glucosides derived from saponins (see WO-94/06402) are also known to this art.

Only rarely do structures result from the grafting of an alkyl chain onto a polyol. However, monopentadecanoylglycerol (see Yokoyama Daisaburo, *Yukagaku* 1995, 44 (4) 266–73), polyalcohol glyceryl ethers, in particular those obtained by condensation of pentaerythritol with pentadecyl glycidyl ether (see JP-08,157,331) and, more particularly, for carbohydrate-derived structures, undecylenyl trehalose (see JP-08,053,326) and alkylpolyglycosides and/or O-acyl glucose derivatives (see WO-93/02657) corresponding to the structure:

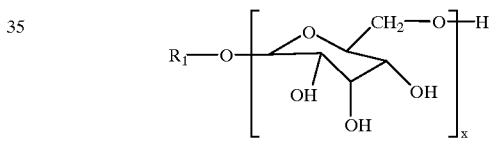

in which $R_1$ is a radical or a mixture of alkyl or alkenyl radicals and/or has the structure:

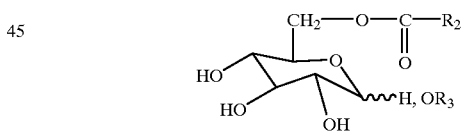

in which $R_2$ is a linear hydrocarbon chain and $R_3$ is hydrogen or a lower $C_1$–$C_4$ alkyl group, have indeed been described. All of these structures, which are carbohydrate-based, differ from those of the invention, hereinbelow more fully described.

Minoxidil® and Aminexil® are also known agents for improving the condition of the hair. Minoxidil, or diamino-2,4-piperidono-6-pyrimidine-3-oxide and derivatives thereof (see U.S. Pat. Nos. 3,461,461, 3,973,061, 3,464,987 and 4,139,619), which are molecules initially known for their anti-hypertensive activity, have also proven to be active in the treatment of hair loss. They stimulate division of the cells which constitute the hair, promote vascularization of the root and, lastly, retard the fibrosis and atrophy of the hair root.

However, although Minoxidil® diminishes hair loss in one-third of patients and effects a slight amount of hair regrowth in another third, it remains ineffective on the other individuals treated. When applied morning and evening in the form of a lotion, it occasionally entails side effects, such as palpitations, a lowering of blood pressure or eczema. Moreover, the hair becomes greasy over the course of this generally permanent treatment.

Aminexil®, which is similar in structure to Minoxidil® (see WO 96/09048), is diamino-2,4-pyrimidine-3-oxide, a molecule capable of combating the production of the principal enzyme responsible for fibrosis. However, this cosmetic compound unfortunately does not act on the other causes of alopecia, namely, the hormonal and vascular factors, which limits its field of application to a fraction of the individuals afflicted with alopecia.

Thus, serious need continues to exist in this art for yet other active compounds for stimulating/inducing hair growth and/or retarding hair loss.

In addition, compounds of the type 2,3-dihydroxypropyl-2-(1-oxoalkyl) amino-2-deoxyglucopyranoside have been formulated into washing compositions for the hair, in particular those having anti-dandruff and hair-conditioning properties (see FR-95/12215).

SUMMARY OF THE INVENTION

It has now unexpectedly and surprisingly been determined that certain deoxyglucopyranoside compounds are conspicuously useful for inducing/stimulating hair growth and/or reducing hair loss in individuals suffering from alopecia.

Briefly, the present invention thus features inducing and stimulating hair growth and/or reducing hair loss, by topically applying to wet hair and to the alopecic regions of the scalp, for periods longer than 2 minutes and preferably longer than 5 minutes, lotions based on 2,3-dihydroxypropyl 2-(1-oxohydrocarbyl)amino-2-deoxyglucopyranoside, the glucopyranoside content of which ranges from 0.1% to 30%.

DETAILED DESCRIPTION OF BEST MODE AND SPECIFIC/PREFERRED EMBODIMENTS OF THE INVENTION

More particularly according to the present invention, the lotions having a low content in active principle are applied without rinsing or with rinsing with water after several hours. The lotions of high concentration are maintained in contact for a few minutes and then removed by rinsing. The applications are daily or twice-daily, the treatment lasting, for average cases, from three to six months; for more severe cases, under the observation of the patient or of the haircare specialist, the treatment may be daily and for life. The subject compositions do not cause any irritation of the scalp, even after prolonged contact without rinsing.

The active principle of the aforesaid lotions is a compound having the structural formula:

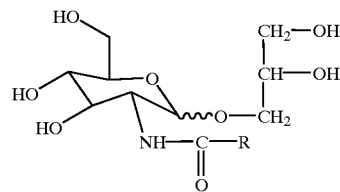

in which R is a linear or branched, saturated or unsaturated hydrocarbon radical having 5–21 carbon atoms, and more particularly 7 to 13 carbon atoms. The 2,3-dihydroxypropyl 2-(1-oxo-10-undecenyl)amino-2-deoxyglucopyranoside derivative is a preferred compound. The synthesis of these compounds is described in French patent application No. 95/12215.

Thus, the present invention also features aqueous/alcoholic lotions containing at least one of the above indicated glucopyranosides, the glucopyranoside constituting 0.1% to 30% by weight relative to the total weight of the composition, more preferably 0.1% to 15%, and even more preferably from 0.25% to 10% for the leave-in compositions, and 2% to 30%, preferably 3% to 15% for the rinse-out compositions. The pH of these compositions advantageously ranges from 3 to 9 and preferably from 4.5 to 7.5.

The aqueous/alcoholic solvents advantageously constitute from 5 to 95% by weight relative to the total weight of the subject compositions, the alcoholic components being cosmetically acceptable products, in particular $C_1$–$C_4$ lower alcohols, glycerol and alkyne glycols.

The subject compositions can also contain other cosmetic or pharmaceutical adjuvants and additives, in order to formulate topical compositions, especially synthetic oils, thickeners, preservatives and basifying or acidifying agents.

Even more effective lotions are formulated by combining the glucopyranoside in synergistic compositions with other compounds which are already known to impove hair growth or to retard hair loss, in particular:

(a) Minoxidil® or similar pyrimidine derivatives described in U.S. Pat. No. 4,139,619; or (b) Aminexil® or similar pyrimidine oxide derivatives described in WO-96/09048, but also;

(c) retinoids such as trans-retinoic acid, isotretinoin, retinol or vitamin A and derivatives thereof, such as the acetate, palmitate or propionate, motretinide, etretinate and zinc trans-retinoate;

(d) antibacterial agents, especially erythromycin;

(e) calcium antagonists such as Cinnarizine and Diltrazem;

(f) hormones such as estriol or analogs thereof, or thyroxin or salts thereof;

(g) antiandrogen agents such as oxendolone or spironolactone;

(h) 5-α-reductase inhibitors;

(i) OH radical scavengers;

(j) dyphylline and salts thereof;

(k) nicotinic acid esters, especially tocopheryl nicotinate, benzyl nicotinate and $C_1$–$C_8$ alkyl nicotinates such as methyl or hexyl nicotinate;

(l) steroidal and non-steroidal anti-inflammatory agents, in particular hydrocortisone and the salts and derivatives thereof, niflumic acid and the like;

(m) citric acid esters, for example tributyl citrate.

Other compounds too can be added, namely, for example, salts, in particular sodium, magnesium, calcium, zinc or copper salts, of aliphatic acids or mixtures thereof, in particular of propionic acid, butyric acid, valeric acid or undecylenic acid, aliphatic acid esters, such as the methyl, ethyl and isopropyl esters, for example undecylenic acid, hydroxycarboxylic or ketocarboxylic acids and esters thereof, salicylic acid and derivatives thereof described in FR-2,581,542, for example salicylic derivatives bearing an alkanoyl radical having from 2 to 12 carbon atoms, cinnamic acid and derivatives thereof, such as, for example, p-β-D-glucopyranosyloxycinnamic acid, substituted cinnamaldehydes such as, for example, p-methoxycinnamaldehyde, ferulic acid, urea, terpenic alcohols such as, for example, thymol, polymers such as, for example, starch, chitosan, chitin, hyaluronic acid, alginates, proteins such as, for example, cereal globular proteins, and the more or less advanced hydrolysis products of these polymers, their complexes with copper, polyamino acids such as, for example, polyglutamates, glycerol esters or polyglycerol esters, in particular mono-, di- or oligoglyceryl fatty acid mono- or diesters, for example mono- or oligoglyceryl cocoates, laurates or undecylenates, polyalcohol ethers especially the glycerol, polyglycerol or pentaerythritol ethers, saccharide monomers, dimers or oligomers such as, for example, glucose, fructose, galactose or trehalose, saccharide esters such as, for example, undecenyl trehalose described in JP-08,053,326, the O-acyl glucose derivatives described in WO-93/02657, glycosides, in particular ergosterol, stigmasterol or stigmastanol glycosides, the alkyl polyglucosides also described in WO 93/02657, lactam forms of saccharides such as, for example, L-arabino-1,5-lactam or D-glucurono-6,3-lactam described in EP-0,334,586, lactones such as D (L) pantolactone, α-pyrones such as those described in EP-0,672,406, such as, for example, 5-methyl-δ-valerolactone, or lactone forms of saccharides, in particular those described in EP-531,111, such as, for example, D-fucono-1,5-lactone, compounds of alkanamido ammonium type such as, for example, an alkanamidotrimethylpropylammonium, a carboxymethylalkanamidodimethylpropylammonium, in particular derived from lauric acid or undecylenic acid or from lauric/myristic fractions, or (3-(docosanamido) propyl) trimethylammonium iodide or (3-(11-(dodecylthio) undecanamido)propyl)-N,N,N-trimethylammonium iodide.

It has also been determined that these compounds influence the bleaching of the hair.

The medium comprising these compositions generally includes glycerol, matrix inherent to its preparation process excluding final purification, water or mixtures of water and of a solvent or mixtures of solvents.

In order to further illustrate the present invention and advantages thereof, the following specific examples are given, it being understood that same are intended only as illustrative and in nowise limitative.

In said examples to follow, the individuals subjected to the experimentation were male volunteers exhibiting accelerated alopecia and the beginning of thinning of the hair and who had not been subjected to any hair treatment for several months.

EXAMPLE 1

A lotion having the following composition was formulated:

(i) 2,3-dihydroxypropyl 2-(1-oxo-10-undecenyl) amino-2-deoxyglucopyranoside 5.0 g (ii) glycerol 20.0 g (iii) ethanol qs 100.0 g (iv) fragrance qs 2 ml of this solution was topically applied to a wet head of hair and to the scalp in the areas afflicted with alopecia, at a frequency of twice per day. A marked slowing of hair loss (noted on brushing) was observed from the 12th week of application and regrowth of hair on the frontal lobes was observed in more than 30% of the individuals from the $6^{th}$ month.

Comment: the 100 g of ethanol can, without any disadvantage, be replaced by a 20/80 propylene glycol/isopropanol mixture.

EXAMPLE 2

The following composition was formulated:

(i) 2,3-dihydroxypropyl 2-(1-oxo-10-undecenyl) amino-2-deoxyglucopyranoside 10.0 g (ii) glycerol 40.0 g (iii) Oramix®NS1 10.0 g (iv) Natrosol® 0.5 g (v) fragrance qs (vi) water qs 100.0 g In this formulation, Oramix®NS10 (SEPPIC) is an alkylpolyglucoside containing three glucose units (hydrophilic portion) and C10/C12/C14 chains (lipophilic portion), in a composition containing 55% active material, with a foaming agent function; Natrosol® is a cetyl- or 2-hexadecyl hydroxyethylcellulose thickener marketed by Aqualon.

Results similar to those described in Example 1 were observed; however, the formula allows more uniform distribution of the product, by means of better foaming.

EXAMPLE 3

The following composition was formulated:

(i) glycerol 40.0 g (ii) Oramix®NS1 10.0 g (iii) Natrosol® 0.5

(iv) fragrance qs (v) water qs 100.0 g

No effect was observed, either on regrowth of the hair or on reducing hair loss, even after six months of daily application of 2 ml of the solution onto wet hair and onto the areas afflicted with alopecia.

EXAMPLE 4

The following composition was formulated:

(i) 2,3-dihydroxypropyl 2-(1-oxo-10-undecenyl) amino-2-deoxyglucopyranoside 3.0 g (ii) glycerol 15.0 g (iii) sodium cocoamphodiacetate containing 38% active material 5.0 g (iv) alginic acid 0.5 g (v) fragrance qs (vi) water qs 100.0 g The sodium cocoamphodiacetate was Miranol®C2M Rhône-Poulenc; the alginic acid was Texamid®778 marketed by Henkel.

Results similar to those described in Example 1 were observed with this formula. The ease of uniform application was the same as for that of Example 2.

EXAMPLE 5

Mixed composition:

The lotion having the following composition was formulated:

(i) 2,3-dihydroxypropyl 2-(1-oxo-10-undecenyl) amino-2-deoxyglucopyranoside 5.0 g (ii) glycerol 20.0 g (iii) Minoxidil® 5.0 g (iv) ethanol qs 100.0 g (v) fragrance qs 2 ml of this solution were topically applied to wet hair and to the areas afflicted with alopecia, at a frequency of two applications per day. The results observed, both in terms of the slowing of hair loss and the regrowth of hair on the frontal lobes, were from about 10% to 20% greater than those observed in Examples 1 and 2.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for inducing/stimulating hair growth or retarding hair loss or both inducing/stimulating hair growth and retarding hair loss on a mammalian subject in need of such treatment, comprising topically applying to the affected hair or scalp of said mammalian subject a hair growth stimulating or hair loss retarding effective amount of at least one 2,3-dihydroxypropyl-2-(1-oxohydrocarbyl) amino-2-deoxyglucopyranoside having the structural formula:

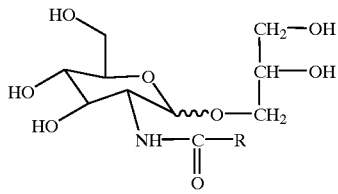

in which R is a linear or branched, saturated or unsaturated hydrocarbon radical having from 5 to 21 carbon atoms.

2. The method as defined by claim 1, wherein said structural formula R is a hydrocarbon radical having from 7 to 17 carbon atoms.

3. The method as defined by claim 2, wherein said structural formula R is a hydrocarbon radical having from 7 to 13 carbon atoms.

4. The method as defined by claim 1, wherein said at least one 2-deoxyglucopyranoside is 2,3-dihydroxypropyl-2-(1-oxo-10-undecenyl)-amino-2-deoxyglucopyranoside.

5. The method as defined by claim 1, comprising topically applying said at least one 2-deoxyglucopyranoside to an alopecic area of the scalp of a human subject.

6. The method as defined by claim 1, comprising topically applying said at least one 2-deoxyglucopyranoside to the wet hair of a human subject.

7. The method as defined by claim 1, comprising maintaining said at least one 2-deoxyglucopyranoside in contact with said affected hair or scalp or both for at least 2 minutes.

8. The method as defined by claim 1, comprising maintaining said at least one 2-deoxyglucopyranoside in contact with said affected hair or scalp or both for at least 5 minutes.

* * * * *